(12) United States Patent
Hayashi et al.

(10) Patent No.: US 7,096,720 B2
(45) Date of Patent: Aug. 29, 2006

(54) HARDNESS TESTER

(75) Inventors: Hirotaka Hayashi, Kure (JP); Takeshi Sawa, Kawasaki (JP); Noriyoshi Ozawa, Kure (JP)

(73) Assignee: Mitutoyo Corporation, Kawasaki (JP)

( * ) Notice: Subject to any disclaimer, the term of this patent is extended or adjusted under 35 U.S.C. 154(b) by 0 days.

(21) Appl. No.: 11/212,620

(22) Filed: Aug. 29, 2005

(65) Prior Publication Data
US 2006/0042362 A1    Mar. 2, 2006

(30) Foreign Application Priority Data
Sep. 1, 2004    (JP)    ............................. 2004-254289

(51) Int. Cl.
G01N 3/48    (2006.01)
G01N 3/00    (2006.01)
G01B 5/00    (2006.01)

(52) U.S. Cl. .................... 73/81; 702/33; 73/78; 73/82; 73/85

(58) Field of Classification Search ................. 73/81; 702/33
See application file for complete search history.

(56) References Cited

U.S. PATENT DOCUMENTS 2,674,874 A * 4/1954 Jones ............................ 73/81
4,331,026 A * 5/1982 Howard et al. ................ 73/81
5,146,779 A * 9/1992 Sugimoto et al. ............. 73/81
2004/0096093 A1* 5/2004 Hauck et al. ................ 382/141
2004/0134263 A1* 7/2004 Tsujii et al. ................... 73/81

FOREIGN PATENT DOCUMENTS

JP          10-132722    *  5/1998
JP        A 10-132722       5/1998

* cited by examiner

Primary Examiner—Hezron Williams
Assistant Examiner—Samir Shah
(74) Attorney, Agent, or Firm—Oliff & Berridge, PLC

(57) ABSTRACT

A hardness tester for measuring hardness of a sample by applying a predetermined test load to the sample with an indenter attached to an indenter attaching member so as to form an indentation on the sample, comprises: the indenter attaching member to which the indenter is attached detachably; the indenter which comprises an identification member with identification information to identify the indenter; an indenter information storing member to store indenter information and the identification information of the indenter, where the indenter information is matched with the respective identification information; an identification information acquiring member to acquire the identification information from the identification member when the indenter is attached to the indenter attaching member; an indenter information acquiring member to acquire the indenter information corresponding to the identification information acquired by the identification information acquiring from the indenter information storing member.

6 Claims, 9 Drawing Sheets

FIG.3

| IDENTIFICATION INFORMATION (53a1) | TYPE OF INDENTER (53a2) | NUMBER (53a3) |
|---|---|---|
| ○○ mA | CONICAL | 1 |
| □○ mA | PYRAMID | 1 |
| □△ mA | PYRAMID | 2 |
| ⋮ | ⋮ | ⋮ |
| △○ mA | SPHERICAL | × × × |

53a / 53a4 (covering 53a2 and 53a3)

FIG.9

| IDENTIFICATION INFORMATION | TYPE OF INDENTER | NUMBER |
|---|---|---|
| ○○ mm | CONICAL | 1 |
| □○ mm | PYRAMID | 1 |
| □△ mm | PYRAMID | 2 |
| ⋮ | ⋮ | ⋮ |
| △○ mm | SPHERICAL | ××× |

HARDNESS TESTER

BACKGROUND OF THE INVENTION

1. Field of the Invention

The present invention relates to a hardness tester to measure hardness of a sample by forming an indentation on the surface of the sample.

2. Description of Related Art

In earlier development, for example, a hardness tester is known, in which a load is applied to the surface of a sample by an indenter so as to form an indentation thereon, and hardness of the sample is measured based on measured size and depth of the formed indentation (for example, see JP 10-132722A).

An indenter used for hardness test has various shapes such as conical, pyramid, and spherical, and they are exchanged according to a type of test, property of a sample and the like. Since a calculation formula to calculate hardness from measured data varies according to the indenter, it is necessary to change the calculation formula when the indenter is changed.

Further, even between indenters of same shape, obtained hardness values include error caused by number of use of the indenter. Therefore, it is necessary to use same indenter to reduce the error among a plurality of measurements. Thus, it is necessary to identify each of the indenters.

In earlier development, indenters of same or different shape are distinguished from each other by means of only visual observation.

However, when shape of an indenter is identified by means of visual observation, a user may misidentify the shape of the indenter in exchanging the indenter or may not find out that a set program or calculation formula is different from that for the currently assembled indenter. Thus, it has been problematic that incorrect hardness value is obtained as a result.

Further, it is difficult to distinguish indenters of same shape as each other, it has been problematic to select an identical indenter.

SUMMARY OF THE INVENTION

One of the objects of the present invention is to provide a hardness tester in which an indenter in use can be easily identified.

According to the first aspect of the invention, a hardness tester for measuring hardness of a sample by applying a predetermined test load to the sample with an indenter attached to an indenter attaching member so as to form an indentation on the sample, comprises:

the indenter attaching member to which the indenter is attached detachably;

the indenter which comprises an identification member with identification information to identify the indenter;

an indenter information storing member to store indenter information and the identification information of the indenter, where the indenter information is matched with the respective identification information;

an identification information acquiring member to acquire the identification information from the identification member when the indenter is attached to the indenter attaching member;

an indenter information acquiring member to acquire the indenter information corresponding to the identification information acquired by the identification information acquiring from the indenter information storing member.

By doing so, the identification information acquiring member acquires the identification information from the identification member when the indenter is attached to the indenter attaching member, and the indenter information acquiring member acquires the indenter information corresponding to the identification information acquired by the identification information acquiring member. Thus, it becomes possible that the indenter is identified only by attaching the indenter to the indenter attaching member, so that the indenter can be easily and reliably identified.

The identification information acquiring member may comprise an eddy current meter to measure an eddy current value at the identification member as the identification information, and a metal material constituting the identification member may vary according to the indenter.

By doing so, the eddy current meter provided to the identification information acquiring member measures the eddy current as the identification information, which varies according to the kind of the metal material constituting the identification member. Since the kind of the metal material of the identification member varies according to the indenter, the eddy current value measured by the eddy current meter varies according to the indenter. Thus, it becomes possible to identify the indenter by the eddy current value measured by the eddy current meter, so that the indenter can be identified easily and reliably.

The identification information acquiring member may comprise: a plurality of electric contact points provided to the indenter attaching member; an electricity providing member to apply current through the indenter and the indenter attaching member in a state that the indenter is attached to the indenter attaching member; and a electric continuity detecting member to detect presence or absence of electric continuity at the electric contact points as the identification information, wherein the identification member comprises an conductive part or an insulated part at a position which corresponds to the electric contact points when the indenter is attached to the indenter attaching member, and number and arrangement of the conductive part and insulated part varies according to the indenter.

By doing so, when the electricity providing member applies current through the indenter and the indenter attaching member in a state that the indenter is attached to the indenter attaching member, the current flows only at the conductive part of the identification member. The electric continuity detecting member can detect the number and arrangement of the continuing electric contact point as the identification information. Since the number and arrangement of the conductive part and insulated part varies according to the indenter, the number and arrangement of conductive part where current flows also varies. Thus, the indenter can be identified easily and reliably.

The identification information acquiring member may comprise a distance meter, wherein the identification member comprises a notch at a position which faces with the distance meter when the indenter is attached to the indenter attaching member, the distance meter measures a distance to the notch as the identification information in a state that the indenter is attached to the indenter attaching member, and depth of the notch varies according to the indenter.

By doing so, the distance meter provided to the identification information acquiring member measures the depth of the notch provided to the identification member of the indenter as the identification information. Since the depth of the notch varies according to the indenter, the depth of the notch measured by the distance meter also varies. Thus, it becomes possible to distinguish the indenter by difference of the depth of the notch measured by the distance meter, so that the indenter can be identified easily and reliably.

The hardness tester may further comprise:

a calculation formula storing member to store a calculation formula which gives hardness value and the indenter information, in which the calculation formula is matched with the respective indenter information, and a calculation formula setting member to extract the calculation formula corresponding to the indenter information acquired by the indenter information acquiring member from the calculation formula storing member, and to set the extracted calculation formula automatically.

By doing so, in addition to the above-described effects, the calculation formula setting member extracts the calculation formula corresponding to the indenter information from the calculation formula storing member, and the extracted calculation formula is set automatically. Thus, it becomes possible to set easily and reliably the calculation formula which corresponds to the type of the indenter.

The hardness tester may further comprise:

a indenter history storing member to store the indenter information and an indenter history data relating use of the indenter, in which the indenter information is matched with the respective indenter history data, and an indenter history updating member to update the indenter history data stored in the indenter history storing member based on an execution of hardness test using the indenter.

By doing so, in addition to the above-described effects, the indenter history updating member updates the indenter history data stored in the indenter history storing member is updated according to an execution of hardness test using the indenter. Thus, it becomes possible to manage the indenter history data such as number of use of the indenter easily and reliably.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein;

FIG. 3 is a view showing a data structure of the indenter data file of the first embodiment of the present invention;

FIG. 9 is a view showing a data structure of the indenter data file of the third embodiment of the present invention.

DETAILED DESCRIPTION OF THE PREFERRED EMBODIMENT

Hereinafter, a best mode for carrying out the present invention will be described with reference to the drawings.

First Embodiment

First, constitution of the hardness tester of the present invention will be described.

Figure 1:
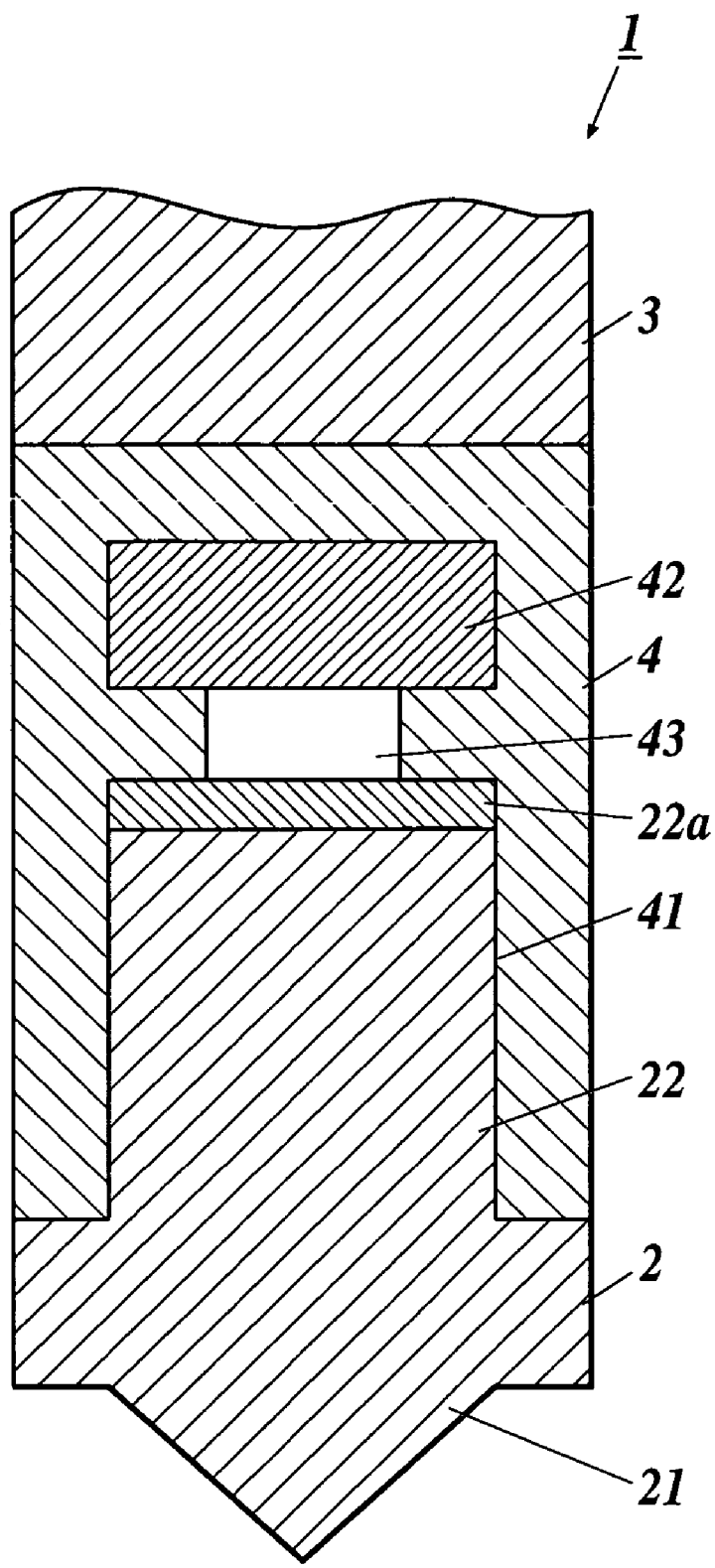
FIG. 1 is a section view schematically showing an assembled constitution of the indenter and indenter attaching member of the first embodiment of the present invention.

As shown in FIG. 1, the hardness tester 1 of the present invention comprises an indenter axis 3 to support an indenter 2, an indenter attaching member 4 to attach the indenter 2 which is installed on a tip of the indenter axis 3, a loading mechanism member (now shown) to apply a predetermined load to the indenter axis in the axial direction thereof, a sample stage (not shown) to mount a sample, and the like.

As shown in FIG. 1, for example, the indenter 2 comprises a indenter main body 21 of various shapes such as conical, pyramid or spherical and an engagement accepting member 22 which engages to an after-mentioned engaging hole 41 of the indenter attaching member 4.

The engagement accepting member 22 comprises an identification member 22a to identify the indenter 2 on the upper side thereof. The identification member 22a is made of various metals and each of the indenters has the identification member 22a of different metal each other.

As shown in FIG. 1, the indenter attaching member 4 comprises an engaging hole 41 to engage the engagement accepting member 22 of the indenter 2, and the indenter 2 is detachably attached inside the indenter attaching member 4.

Further, inside the indenter attaching member 4, an after-mentioned eddy-current meter 42 is housed on the upper part of the engaging hole 41. An aperture 43 is formed between the engaging hole 41 and the eddy current meter 42.

Figure 2:
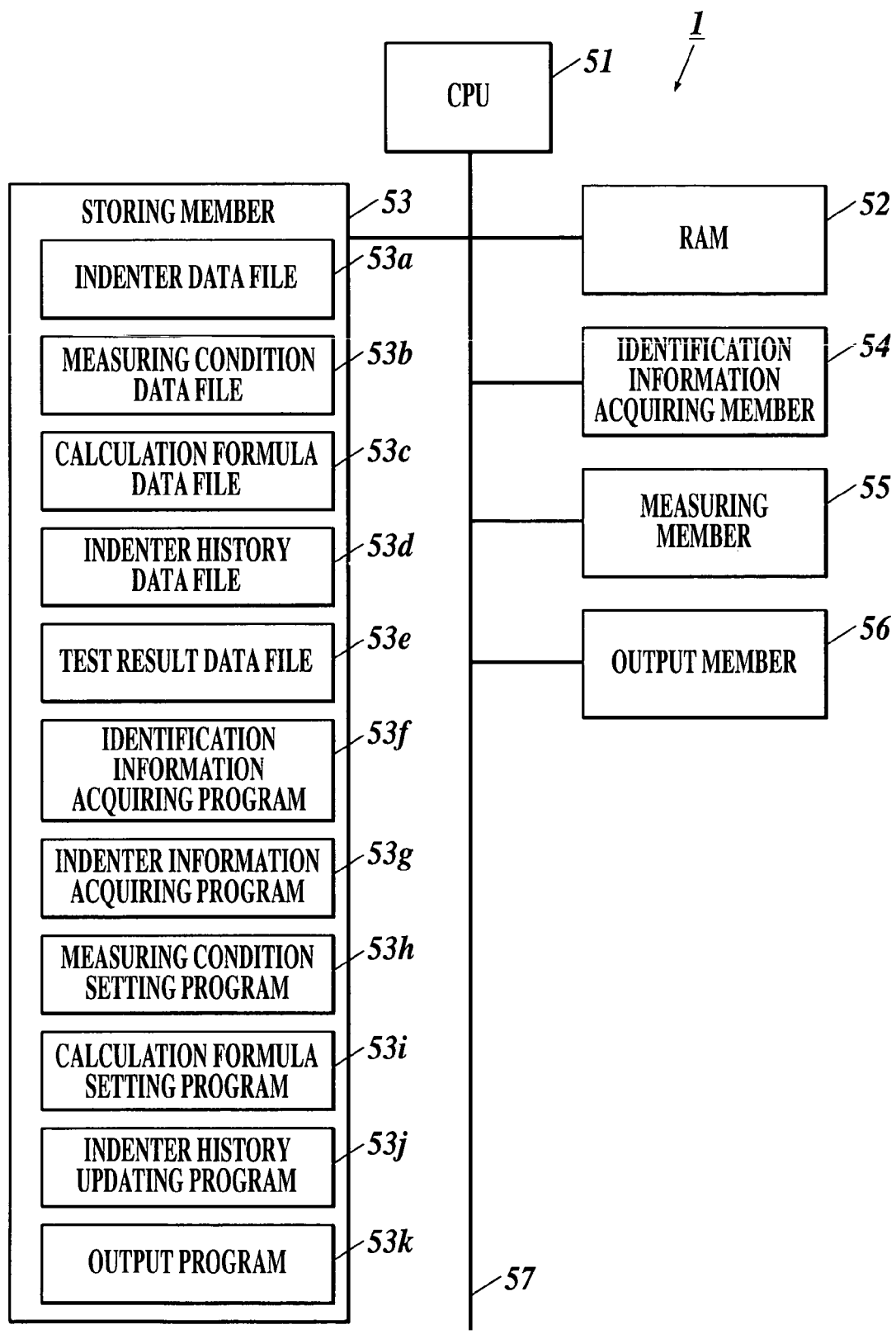
FIG. 2 is a block diagram showing a main constitution of the hardness tester of the first embodiment of the present invention.

Further, as shown in FIG. 2, for example, the hardness tester 1 comprises a CPU (Central Processing Unit) 51, a RAM (Random Access Memory) 52, a memory 53, an identification information acquiring member 54, a measuring member 55, an output member 56 and the like. These members are connected by bus 57 with each other.

The CPU 51 performs various controlling operations according to various processing programs stored in the memory 53.

More specifically, the CPU 51 identifies the indenter 2 based on identification information 53a1 output from the identification information acquiring member 54, and sets a measuring condition, calculating formula and the like which correspond to the type of the identified indenter. Further, the CPU 51 calculates a hardness value based on the measured data output from the measuring member 55, and stores it to the memory 53. Further, CPU 51 updates an indenter history data file 53d stored in the memory 53.

RAM 52 expands the processing program or the like executed by the CPU 51 to a program storing area of the RAM 52, along with storing input data and a processing result or the like generated in executing the processing program in a work area.

The memory 53 comprises recording medium (not shown) where a program, data and the like are previously stored. The recording medium is composed of magnetic or optical recording medium or a semiconductor memory. As shown in FIG. 2, for example, the memory 53 stores an indenter data file 53a as an indenter information storing member, a measuring condition data file 53*b* as a measuring condition storing member, a calculation formula data file 53*c* as a calculation formula storing member, an indenter history data file 53*d* as an indenter history storing member, a test result file 53*e* as a test result storing member, an identification information acquiring program 53*g* as an identification information acquiring member, a measuring condition setting program 53*h* as a measuring condition setting member, a calculation formula setting program 53*i* as a calculation formula setting member, an indenter history updating program 53*j* as an indenter history updating member, and an output program 53*k* and the like.

As shown in FIG. 3, for example, the indenter data file 53*a* is stored in which an identification information 53*a*1 output from the identification information acquiring member 54 corresponds to an indenter information 53*a*4 including a type 53*a*2 and a number 53*a*3 of the indenter 2. The type of the indenter 2 includes cone, pyramid, cylinder or the like. The number of the indenter 2 is a sequential number or the like to distinguish each of the indenters 2. Each indenter information 53*a*4 is matched with different identification information 53*a*1.

The measuring condition data file 53*b* is, for example, stored in which measuring condition data such as set load is matched with the corresponding indenter information 53*a*4.

The calculation formula data file 53*c* is, for example, stored in which calculation formula data is matched with the corresponding indenter information 53*a*4.

The test result file 53*e* is data file to record a measured value obtained in the measuring member 55, a hardness value calculated from the measured value by the after-mentioned calculation formula setting member and the like.

The indenter history data file 53*d* is data file in which the indenter information 53*a*4 is matched with the indenter history data. Once the indenter 2 is used in the hardness tester 1, the CPU 51 executes the after-mentioned indenter history updating program 53*j* so that the indenter history data is rewritten and the indenter history data file 53*d* is updated.

The identification information acquiring program 53*f* is, for example, a program to acquire the identification information 53*a*1 from the identification member 22*a*. More specifically, the identification information acquiring program 53*f* controls the identification information acquiring member 54 to acquire the identification information 53*a*1 from the identification member 22*a*, and to output said identification information 53*a*1 to the CPU 51. The CPU 51 works as a part of the identification information acquiring member by executing the identification information acquiring program 53*f*.

The indenter information acquiring program 53*g* is, for example, a program to acquire the indenter information 53*a*4 from the above-described indenter data file 53*a* based on the indenter information 53*a*1, and more specifically, is a program to refer to the indenter data file 53*a* based on the identification information 53*a*1 acquired by the CPU 51 and to acquire the indenter information 53*a*4 corresponding to said identification information 53*a*1. The CPU 51 works as the indenter information acquiring member by executing the indenter information acquiring program 53*g*.

The measuring condition setting program 53*h* is, for example, a program to set a measuring condition corresponding to the indenter information 53*a*4, and more specifically is a program to extract a measuring condition corresponding to the indenter information 53*a*4 acquired by the CPU 51 from the measuring condition data file, to control the measuring member 55 based on the extracted measuring condition data, to make the measuring member 55 measure a sample, to output the measured value to the CPU 51. The CPU 51 works as the measuring condition setting member by executing the measuring condition setting program 53*h*.

The calculation formula setting program 53*i* is, for example, a program to calculate a hardness value from the measured value with a calculating formula corresponding to the indenter information 53*a*4, and more specifically, is a program to extract the calculation formula corresponding to the indenter information 53*a*4 acquired by the CPU 51 from the calculation formula data file 53*c*, to calculate a hardness value from a measured value data output from the measuring member 55 with the extracted calculation formula data, and to record the indenter information 53*a*4, calculation formula data and test result including the measured value and hardness value to the test result file 53*e*. The CPU works as the calculation formula setting member by executing the calculation formula setting program 53*i*.

The indenter history updating program 53*j* is, for example, a program to update indenter history data, and more specifically, to rewrite the indenter history data such as number of use recorded in the indenter history data file 53*d* so as to update the indenter history data file 53*d* once the indenter 2 is used in the hardness tester 1. The CPU 51 works as the indenter history updating member by executing the indenter history updating program 53*j*.

The output program 53*k* is, for example, a program to output the test result, indenter history data and the like at the output member, and more specifically, is a program to extract the indenter information 53*a*4, calculation formula and test result from the test result file 53*e*, to extract the indenter history data from the indenter history data file 53*d*, and to output the extracted indenter information 53*a*4, calculation formula data, test result and indenter history data at the output member 56.

The identification information acquiring member 54 has a function to acquire identification information from the identification member 22*a*, and works as a part of the identification information acquiring member. The identification acquiring member 54 includes the eddy current meter 42 and the like housed on the upper part of the engaging hole 41 of the indenter attaching member 4. The eddy current meter 42 measures a value of eddy current generated by placing an object such as metal at a predetermined distance. The value of the generated eddy current varies according to kind of the metal.

When the indenter 2 is attached on the engaging hole 41 of the indenter attaching member 4, the eddy current meter 42 measures the eddy current. Since the material of the indenter engagement accepting member 22 varies according to the indenter 2 to be attached, the value of the measured eddy current varies according to the indenter 2. The identification information acquiring member 54 acquires the value of the eddy current measured by the eddy current meter 42 as the identification information 53*a*1. That is, as shown in FIG. 3, in the present embodiment for example, the measured eddy current value represents the identification information 53*a*1.

The measuring member 55 comprises, for example, a member to measure a diagonal length of an indentation on a sample formed by the pyramid indenter 2 (not shown).

The output member 56 comprises a sheet feeding member (not shown), sheet ejecting member (not shown) and the like, and extracts the indenter information 53*a*4, calculation formula data and test result from test result file 53*e*, extracts the indenter history data from indenter history data file 53*d*, and outputs them to a paper. Thus, it works as the output member. Output system of the output member 56 may be any system such as ink-jet system, thermal transfer system, laser system, sublimation system, TA system or the like.

Next, operation of the hardness tester 1 having the above-described constitution will be explained.

Figure 4:
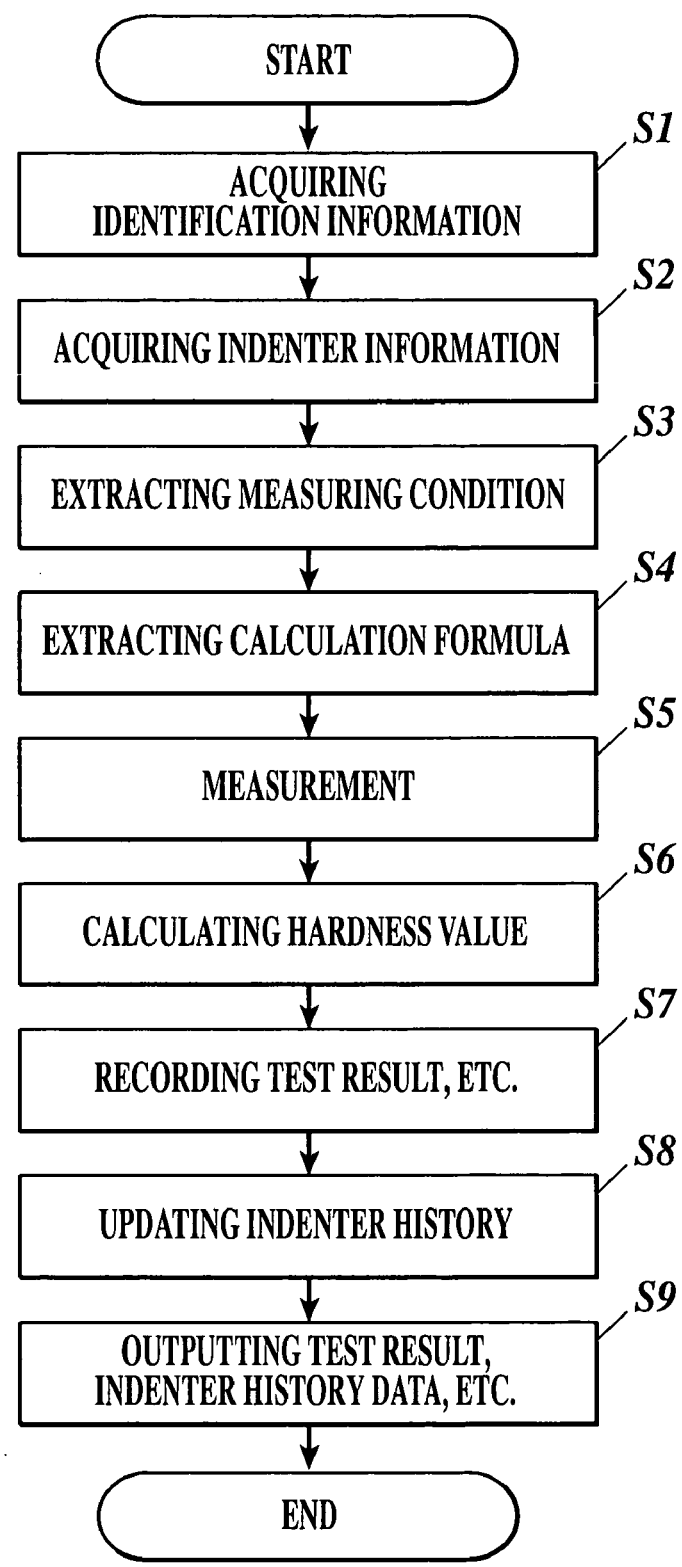
FIG. 4 is a flowchart showing an operation of the hardness tester of the first embodiment of the present invention.

First, as shown in FIG. 4, the indenter 2 is attached to the indenter attaching member 4 of the hardness tester 1. Then, the CPU 51 controls the identification information acquiring member 54 by executing the identification information acquiring program 53f, so that the identification information 53a1 is acquired from the identification member 22a of the indenter 2 (step 1). More specifically, the CPU 51 controls the identification information acquiring member 54 so that the eddy current meter 42 measures a value of eddy current generated by the indenter 2 attached on the indenter attaching member 4, and makes the identification information acquiring member 54 output the value of the measured eddy current as the identification information 53a1 to the CPU 51.

Next, the CPU 51 executes the indenter information acquiring program 53g so as to refer to the indenter data file 53a and to acquire the indenter information 53a4 corresponding to the output identification information 53a1 from the identification information acquiring member 54 Next, the CPU 51 executes the measuring condition setting program 53h so as to extract measuring condition data corresponding to the acquired indenter information 53a4 from the measuring condition data file 53b (step S3). Further, the CPU 51 extracts the calculation formula data corresponding to the acquired indenter information 53a4 from the calculation data file 53c (step S4).

Then, the CPU 51 executes the measuring condition setting program 53h so as to control the measuring member 55 based on the extracted measuring condition data, to measure a sample at the measuring member 55 and to output the measured value to the CPU 51 (step S5).

Next, the CPU 51 executes the calculation formula setting program 53i so as to calculate hardness value from the measured value output from the measuring member 55 with the extracted calculation formula data (step S6), and to record the test result including the indenter information 53a4, calculation formula data, measured value, hardness value and the like to the test result file 53e (step S7).

Next, the CPU 51 executes the indenter history updating program 53j so as to rewrite indenter history data such as number of use recorded on the indenter history data file 53d stored in the memory 53 once the indenter 2 is used in the hardness tester 1. Thus, the CPU 51 updates the indenter history data file 53d (step S8).

Next, the CPU 51 executes the output program 53k so as to extract the indenter information 53a4, calculation formula data and test result from the test result file 53e and to extract the indenter history data from the indenter history data file 53d. The CPU 51 outputs the extracted test result and indenter history data to the output member 56 and controls the output member 56 so as to output said indenter information 53a4, calculation formula data and test result and the indenter history data (step S9).

In the present embodiment, the eddy current meter 42 is housed on the upper part of the engaging hole 41. However, the position of the eddy current meter 42 is not limited thereto. The eddy current meter can be located anywhere if there is a certain distance between the eddy current meter and the indenter 2 and it is possible to measure the eddy current generated by the indenter 2. For example, it can be installed on the side of the indenter attaching member 4.

According to the above-described hardness tester 1 of the present invention, the CPU 51 executes the identification information acquiring program 53f so as to control the eddy current meter 42 and to acquire the identification information 53a1 from the identification member 22a when the indenter 2 is attached to the indenter attaching member 4, and executes the indenter information acquiring program 53g so as to acquire the corresponding indenter information 53a4 from the indenter data file 53a based on the identification information 53a1. Thus, it becomes possible to identify the indenter 2 automatically by only attaching the indenter 2 on the indenter attaching member 4 so that the indenter 2 is easily and reliably identified.

Further, the CPU 51 executes the calculation formula setting program 53i so as to refer to the calculation formula 53c, to extract the calculation formula corresponding to the indenter information 53a4 and to set it automatically. Thus, it becomes possible to set the calculation formula matched to each indenter 2 easily and reliably.

Further, the CPU 51 executes the indenter history updating program 53j so as to update the indenter history data stored in the indenter history data file 53d based on the execution of the hardness test with the indenter 2. Thus, it becomes possible to manage the indenter history data such as number of use of the indenter 2 easily and reliably.

Second Embodiment

First, a constitution of a hardness tester 1A of the second embodiment of the present invention will be described.

Figure 5:
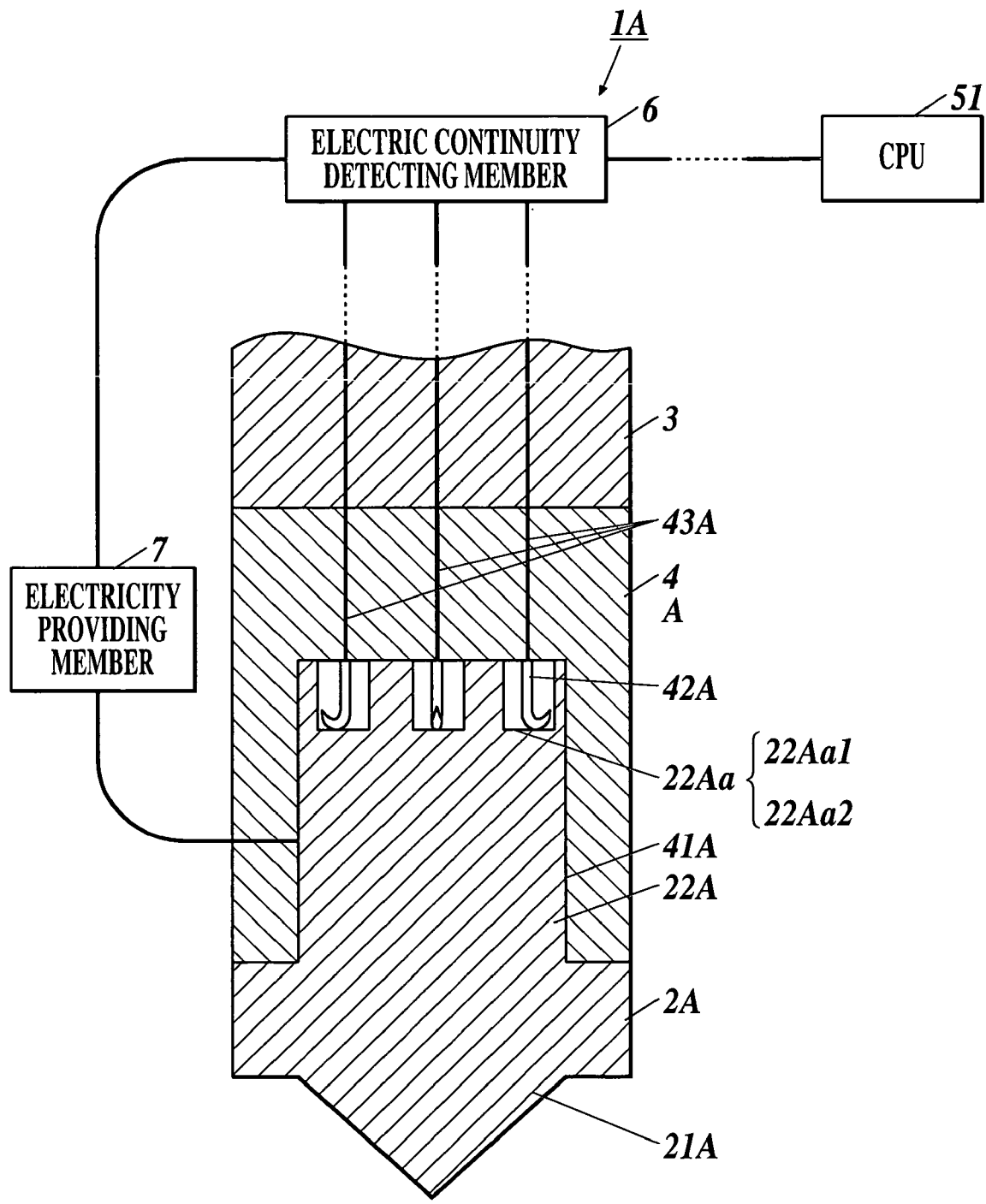
FIG. 5 is a section view showing an assembled constitution of the indenter and indenter attaching member and the identification information acquiring member of the second embodiment of the present invention.

The hardness tester 1A of the second embodiment of the present invention is different from the hardness tester of the first embodiment only in the point of constitution of the indenter attaching member 4A and the indenter 2A, as shown in FIG. 5. Thus, the identical reference numerals are given to the same compositions as the first embodiment, and the descriptions thereof are omitted.

The indenter 2A of the second embodiment is, for example as shown in FIG. 5, composed of an indenter main body 21A of various shapes such as conical, pyramid or spherical, and an engagement accepting member 22A which engages to an engaging hole 41A of an after-mentioned indenter attaching member 4A.

Figure 6A:
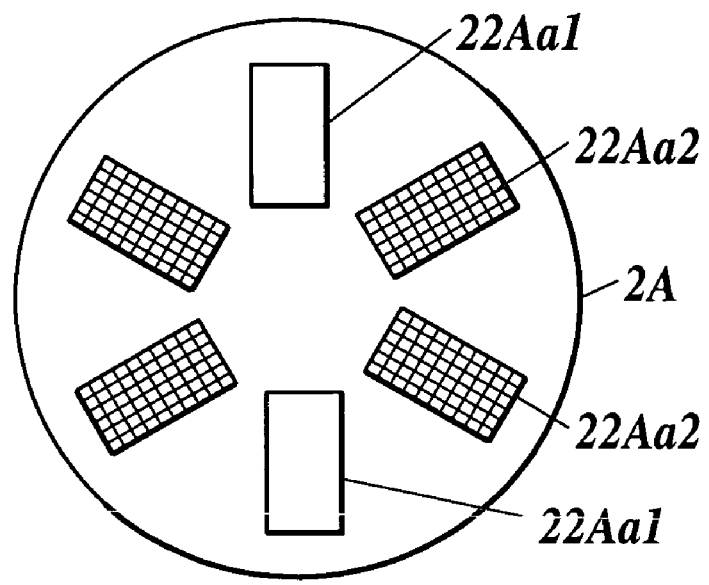
FIG. 6 is a top view of the indenter of FIG. 5.
Figure 6B:
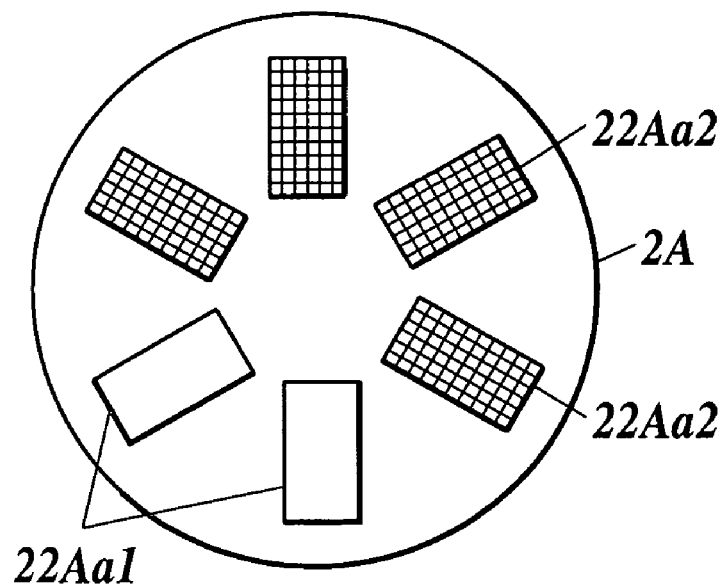

The indenter accepting member 22A is made of a conductive material, and comprises an identification member 22Aa to identify the indenter 2A. The identification member 22Aa comprises a plurality of conductive hole 22Aa1 (conductive area) and insulated hole 22Aa2 (insulated area) which an after-mentioned spring contact 42A provided on a ceiling plane of the engaging hole 41A of the indenter attaching member 4A is inserted to and contact with. FIGS. 6A and 6B shows a view watching from the upper side in which the hatching represents the insulated hole 22Aa2. As shown in FIGS. 6A and 6B, the number and arrangement of the conductive hole 22Aa1 and insulated hole 22Aa2 varies according to the indenter 2A.

The indenter attaching member 4A comprises the engaging hole 41A inside the indenter attaching member 4A, to which the engagement accepting member 22A of the indenter 2A engages. The indenter of various shapes such as conical, pyramid or spherical are detachably attached thereto.

Further, a plurality of the spring contacts 42A, . . . are attached to the ceiling plane of the engaging hole 41A as a part of the identification information acquiring member. Signal lines 43A, . . . are connected with these respective spring contacts. Each signal line 43A is connected with CPU 51 and a electricity providing member 7.

The electric continuity detecting member 6 comprises a detection circuit or the like, and detects presence or absence of conductivity at each of the spring contacts 42A, . . . and output it to the CPU 51. The electric continuity detecting member 6 works as the electric continuity detecting member.

The electricity providing member 7 is electrically connected with the engagement accepting member 22A when the indenter 2A is attached to the indenter attaching member 4A. The electricity providing member 7 works as a current carrier to apply current through the indenter 2A and indenter accepting member 4A in a state that the indenter 2A is attached to the indenter attaching member 4A.

The identification information acquiring member 54A has a function to acquire the identification information 53a5 from the identification member 22Aa, and works as a part of the identification information acquiring member. The identification information acquiring member 54A comprises the electricity providing member 7, electric continuity detecting member 6 and the like as well as the above-described spring contacts 42A and signal lines 43A.

Figure 7:
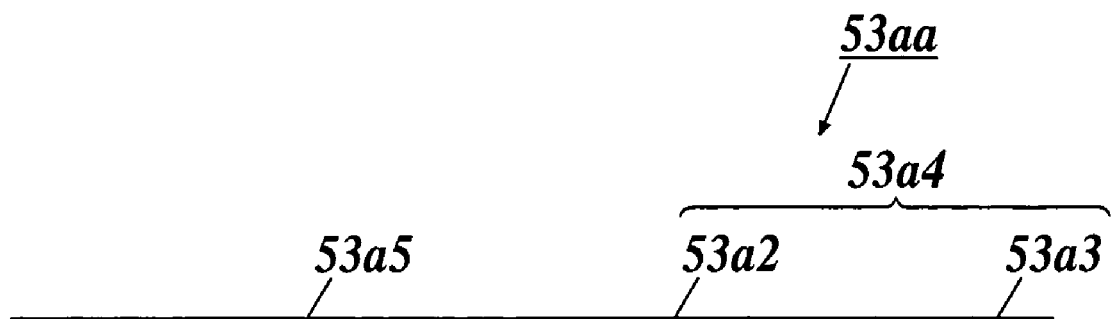
FIG. 7 is a view showing a data structure of the indenter data file of the second embodiment of the present invention.

When the indenter 2A is attached to the engaging hole 41A of the indenter attaching member 4A so as to apply current from the electricity providing member 7, current is applied from the electricity providing member 7 to the engagement accepting member 22A. Thus, the current flows only through the signal lines 43A and spring contacts 42A connected with the conductive hole 22Aa1. Since the number and arrangement of the conductive hole 22Aa1 varies according to the indenter 2A to be attached, the number and arrangement of the conductive hole 22Aa1 where current flows also varies according to the indenter 2A. Then, the identification information acquiring member 54A detects from the electric continuity detecting member the number and arrangement of the conductive hole 22Aa1 where current flows, acquires it as the identification information 53a5, and output it to CPU 51. That is, as shown in FIG. 7 for example, in the present embodiment, the identification information 53a5 of the indenter data file 53aa is represented by the arrangement of the conductive hole 22Aa1 where current flows.

Next, an operation of the above-described hardness tester 1A of the second embodiment will be described.

First, the indenter 2A is attached to the indenter attaching member 4A of the hardness tester 1A. Next, the CPU 51 executes the identification information acquiring program 53f so as to control the identification information acquiring member 54A and to acquire the identification information 53a5 from the identification member 22Aa of the indenter 2A. More specifically, the CPU 51 controls the identification information acquiring member 54A to acquire the number and arrangement of the conductive holes 22Aa1 where current flow as the identification information 53a5, and to output the identification information 53a5 to the CPU 51.

Hereafter, similar operation with that for the hardness tester 1 of the first embodiment is conducted.

In the present embodiment, the conductive hole 22Aa1 and spring contact are exemplified for the conductive area conductive contact point. Thus, they are not limited thereto, and any member which can be connected electrically can be given.

According to the above-described hardness tester 1A of the second embodiment of the present invention, the identification information acquiring member 54A comprises a plurality of the spring contacts 42A provided with the indenter attaching member 4A and the electricity providing member 7 and the identification member 22Aa comprises the conductive hole 22Aa1 or insulated hole 22Aa2 at a position corresponding to the spring contacts 42a when the indenter 2A is attached to the indenter attaching member 4A. Thus, when the indenter 2A is attached to the indenter attaching member 4A and the electricity providing member 7 applies current, the current flows only the signal line 43A and spring contact 42A which are connected with the conductive hole 22Aa1, which makes it possible to detect the number and arrangement of the conductive spring contacts 42A as the identification information 53a5. Thus, the number and arrangement of the conductive hole 22Aa1 where current flows varies when the number and arrangement of the conductive hole 22Aa1 and insulated hole 22Aa2 varies according to the indenter 2A. As a result, it becomes possible to identify the indenter 2A according to difference of the number and arrangement of the conductive holes 22Aa1 where current flows, so that the indenter 2A is easily and reliably identified.

Third Embodiment

First, a hardness tester 1B of the third embodiment of the present invention will be described.

Figure 8:
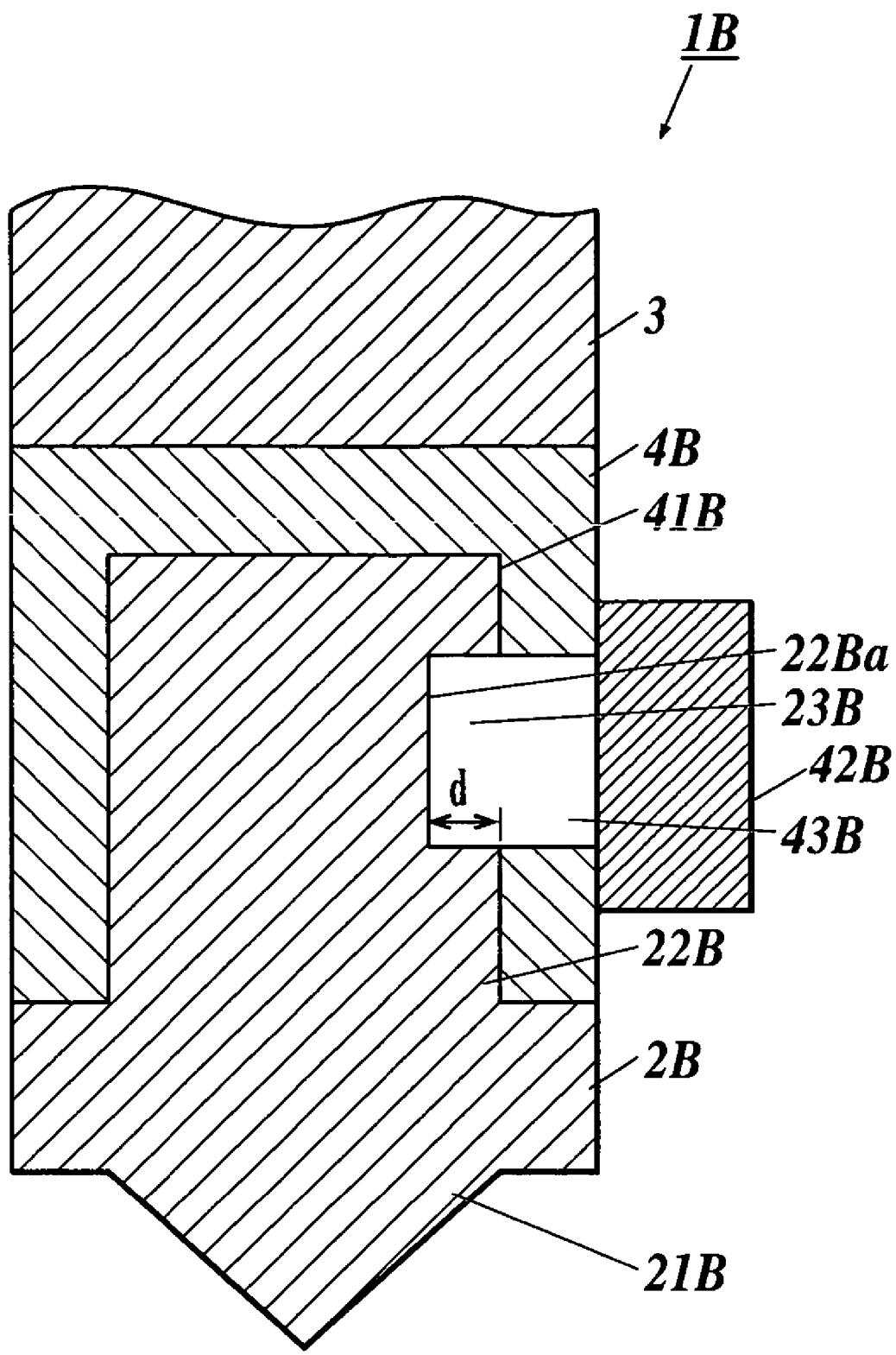
FIG. 8 is a section view schematically showing an assembled constitution of the indenter and indenter attaching member of the third embodiment of the present embodiment.

As shown in FIG. 8, the hardness tester 1B of the third embodiment of the present invention differs from the hardness tester 1 of the first embodiment only in the point of constitution of the indenter attaching member 4B and indenter 2B. Thus, the identical reference numeral is given to the same composition as the first embodiment, and the descriptions thereof are omitted.

The indenter 2B of the second embodiment is, for example as shown in FIG. 8, composed of an indenter main body 21B of various shape such as conical, pyramid and spherical, and an engagement accepting member 22B which engages to an engaging hole 41B of an after-mentioned indenter attaching member 4B.

The engagement accepting member 22B comprises an identification member 22Ba to identify the indenter 2B at the side thereof. A notch 23B is provided to the identification member 22Ba. When the indenter 2B is attached to the indenter attaching member 4B, the notch 23B faces with an after-mentioned distance meter 42B provided to the side of the indenter attaching member 4B. The depth d of the notch 23B varies according to each indenter 2B.

The indenter attaching member 4B comprises an engaging hole 41B to engage the engagement accepting member 22B of the indenter 2B inside the indenter attaching member 4B. The indenter 2B of various shapes such as conical, pyramid and spherical are detachably attached thereto.

A through hole 43B is provided at the side of the indenter attaching member 4B, and a distance meter 42B is provided outside the through hole 43B.

The identification information acquiring member 54B has a function to acquire the identification information 53a6 from the identification member 22Ba, and works as a part of the identification information acquiring member. The identification acquiring member 54B comprises the distance meter 42B and the like provided at the side of the indenter attaching member 4B.

The distance meter 42B is, for example, an optical distance meter.

When the indenter 2B is attached to the engaging hole 41B of the indenter attaching member 4B, the distance meter 42B emits light to the notch 23B and counts the entering time of reflected light reflected on the notch 23B. Since the depth d of the notch 23B varies according to the indenter 2B to be attached, the time counted by the distance meter 42B varies according to the indenter 2B to be attached. Then, the identification information acquiring member 54B acquires the depth d which is calculated from the time counted by the distance meter 42B as the identification information 53a6. That is, in the present embodiment, the identification information 53a6 of the indenter data file 53ab is, for example, represented by the depth d of the notch 23B measured by the distance meter 42B, as shown in FIG. 9.

Next, operation of the hardness tester 1B of the third embodiment as described above will be described.

First, the indenter 2B is attached to the indenter attaching member 4B of the hardness tester 1B. Next, the CPU 51 executes the identification information acquiring program 53f so as to control the identification information acquiring member 54B, and to make the identification information acquiring member 54B acquire the identification information 53a6 from the identification member 22Ba of the indenter 2B. More specifically, the CPU 51 controls the identification information acquiring member 54B to acquire the depth d of the notch 23B measured by the distance meter 42B as the identification information 53a6, and to output the identification information 53a6 to the CPU 51.

Hereafter, similar operation with that for the hardness tester 1 of the first embodiment is conducted.

In the third embodiment of the present invention, a meter to measure a distance by light is exemplified as the distance meter. However, the distance meter may be any meter which can measure the depth of the notch 23B of the indenter 2B. For example, a distance meter to measure a distance by eddy current can be given.

According to the hardness tester 1B of the third embodiment of the present invention, the identification information acquiring member 54B comprises the distance meter 42B provided to the indenter attaching member 4B, the identification member 22Ba comprises the notch 23B. The distance meter 42B measures the depth d of the notch 23B provided to the identification member 22Ba of the indenter 2B as the identification information 53a6. Since the depth d of the notch 23B varies according to the indenter 2B, the depth d measured by the distance meter 42B also varies. Thus, the indenter 2B can be distinguished from the difference of the depth d of the notch 23B measured by the distance meter 42B, so that it becomes possible to identify the indenter 2B easily and reliably.

The identification member and identification information acquiring member of the present invention is not limited to the composition disclosed in the above embodiments, but any identification information acquiring member can be given if it comprises an identification member with identification information by which each indenter can be identified and a member which can acquire the identification information from the identification member.

Further, the hardness tester 1 of the present invention may comprise an indenter history searching program to search the indenter history data file to extract the indenter history data (not shown). The CPU 51 can execute the indenter history searching program so as to extract the indenter history data such as the number of uses of the indenter from the indenter history data file. By doing so, a user can check the indenter use history data easily. Thus, for example, when accuracy of a measured hardness value is estimated with the number of uses of the indenter or the like, the user can easily check the indenter history data such as the number of uses of the indenter. The CPU 51 can work as the indenter history searching member by executing the indenter history searching program.

The entire disclosure of a Japanese Patent Application No. Tokugan 2004-254289 filed on Sep. 1, 2004, including specifications, claims, drawings and summaries are incorporated herein by reference in their entirety.

What is claimed is:

1. A hardness tester for measuring hardness of a sample by applying a predetermined test load to the sample with an indenter attached to an indenter attaching member so as to form an indentation on the sample, comprising:

the indenter attaching member to which the indenter is attached detachably;

the indenter which comprises an identification member with identification information to identify the indenter;

an indenter information storing member to store indenter information and the identification information of the indenter, where the indenter information is matched with the respective identification information;

an identification information acquiring member to acquire the identification information from the identification member when the indenter is attached to the indenter attaching member;

an indenter information acquiring member to acquire the indenter information corresponding to the identification information acquired by the identification information acquiring member from the indenter information storing member.

2. The hardness tester as claimed in claim 1, wherein the identification information acquiring member comprises an eddy current meter to measure an eddy current value at the identification member as the identification information, and a metal material constituting the identification member varies according to the indenter.

3. The hardness tester as claimed in claim 1, wherein the identification information acquiring member comprises: a plurality of electric contact points provided to the indenter attaching member; an electricity providing member to apply current through the indenter and the indenter attaching member in a state that the indenter is attached to the indenter attaching member; and a electric continuity detecting member to detect presence or absence of electric continuity at the electric contact points as the identification information, wherein the identification member comprises an conductive part and an insulated part at a position which corresponds to the electric contact points when the indenter is attached to the indenter attaching member, and number and arrangement of the conductive part and insulated part varies according to the indenter.

4. The hardness tester as claimed in claim 1, wherein the identification information acquiring member comprises a distance meter, the identification member comprises a notch at a position which faces with the distance meter when the indenter is attached to the indenter attaching member, the distance meter measures a distance to the notch as the identification information in a state that the indenter is attached to the indenter attaching member, and depth of the notch varies according to the indenter.

5. The hardness tester as claimed in claim 1, further comprising:

a calculation formula storing member to store a calculation formula which gives hardness value and the indenter information, in which the calculation formula is matched with the respective indenter information, and a calculation formula setting member to extract the calculation formula corresponding to the indenter information acquired by the indenter information acquiring member from the calculation formula storing member, and to set the extracted calculation formula automatically.

6. The hardness tester as claimed in claim 1, further comprising:

a indenter history storing member to store the indenter information and an indenter history data relating use of the indenter, in which the indenter information is matched with the respective indenter history data, and an indenter history updating member to update the indenter history data stored in the indenter history storing member based on an execution of a hardness test using the indenter.

* * * * *